United States Patent [19]

Marinkovich et al.

[11] Patent Number: 4,558,013

[45] Date of Patent: Dec. 10, 1985

[54] CALIBRATED REACTION MEASUREMENT SYSTEM

[75] Inventors: Vincent A. Marinkovich, Palo Alto; David H. Riege, Newark; John W. Dyminski, Cupertino, all of Calif.

[73] Assignee: Mast Immunosystems, Ltd., Mountain View, Calif.

[21] Appl. No.: 483,292

[22] Filed: Apr. 8, 1983

[51] Int. Cl.$^4$ .................. G01N 33/58; G01N 21/00
[52] U.S. Cl. .................. 436/513; 436/535; 436/804; 436/805; 436/806; 436/807; 436/808; 436/809; 435/4; 435/7; 422/56; 422/57; 422/58; 422/61; 422/68; 422/71
[58] Field of Search .............. 435/4, 7; 436/513, 535, 436/804, 805–809; 422/56–58, 61, 68, 71

[56] References Cited

U.S. PATENT DOCUMENTS

| | | | |
|---|---|---|---|
| 3,941,876 | 3/1976 | Marinkovich | 436/530 |
| 4,031,197 | 6/1977 | Marinkovich | 436/542 |
| 4,211,762 | 7/1980 | Huggins et al. | 436/513 |
| 4,235,865 | 11/1980 | Thoma | 436/535 |
| 4,256,833 | 3/1981 | Ali et al. | 436/513 |
| 4,331,650 | 5/1982 | Brewer et al. | 436/524 |
| 4,459,360 | 7/1984 | Marinkovich | 436/808 |
| 4,486,540 | 12/1984 | Brewer et al. | 436/513 |

*Primary Examiner*—Christine M. Nucker
*Attorney, Agent, or Firm*—Fulwider, Patton, Rieber, Lee & Utecht

[57] ABSTRACT

Method and apparatus for use in accurately measuring the binding reactions occurring between a predetermined class of components in a liquid specimen and their corresponding binding conjugates coated on separate test regions of a carrier. The carrier further includes a reference region that is uncoated, and the carrier is adapted for simultaneous contact of all of its regions with the liquid specimen. Any resulting binding reaction on each test region indicates both specific binding to the coated component as well as non-specific binding, and any resulting binding reaction on the reference region indicates merely non-specific binding. The measurements for the test regions are all reduced by an amount determined in accordance with the measurement for the reference region, to reduce the effects of non-specific binding on those measurements and thereby provide accurate measurements of the specific binding on each coated component.

27 Claims, 5 Drawing Figures

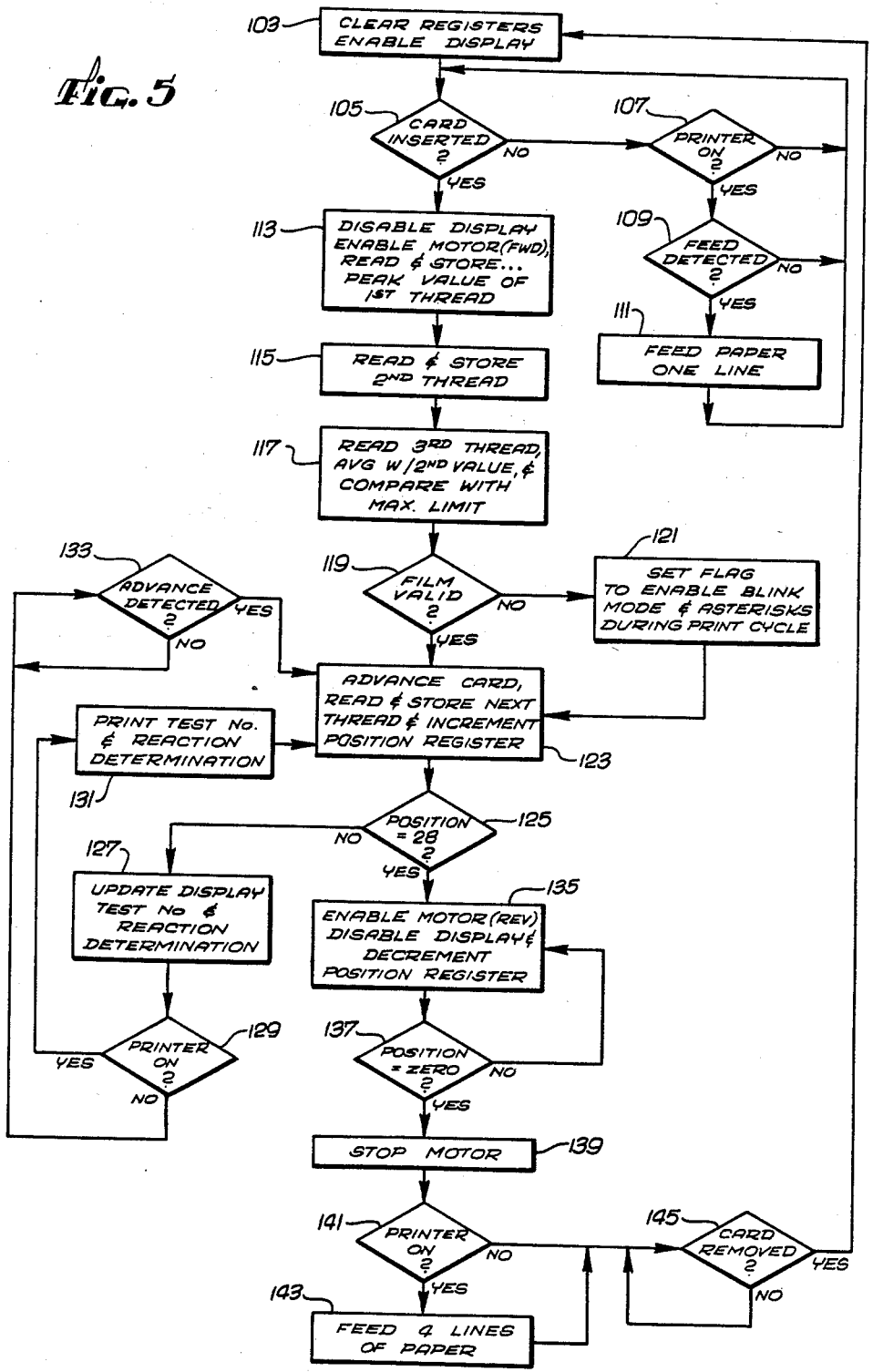

CALIBRATED REACTION MEASUREMENT SYSTEM

BACKGROUND OF THE INVENTION

This invention relates generally to systems for measuring the magnitudes of reactions occurring between a predetermined class of components in a liquid specimen and their corresponding conjugates coated on a carrier, and, more particularly, to systems of this kind having means for correcting for the effects of background noise and non-specific reactions of the components to the carrier.

Systems of this general type are of particular use in immunological applications. For example, an insoluble carrier coated with a known quantity of a single antigen or antibody can be incubated with a liquid specimen to determine the presence in the specimen of a conjugate for the coating, i.e., the corresponding antibody or antigen. In some systems, a number of separate binding components, particularly antigens, are coated on spaced regions of a cellulosic carrier, for simultaneous incubation with a single liquid specimen.

After incubation, the magnitudes of any resulting reactions are measured to determine the concentration of antigen-specific antibodies in the specimen. These measurements can be made using techniques like radioimmunoassay, in which the carrier is incubated with a liquid containing radioactively-tagged antibodies that bind to any antibody previously bound to the antigen-coated carrier. The presence of any radioactivity on a particular region of the carrier can then be measured, for example, by means of a gamma counter, or, alternatively, by exposing photographic film and then measuring the optical density of a resulting photographic print. A copending and commonly-assigned application for U.S. Patent, Ser. No. 308,935, filed in the name of Vincent A. Marinkovich and entitled "Multiple-Component Binding Assay System And Method Of Making And Using It" now issued as U.S. Pat. No. 4,459,360, describes this incubation and measurement technique in greater detail.

Although the technique described above for measuring the magnitudes of reactions has proven generally effective, it is not believed to be as accurate as is possible. This is due, in large part, to the effects of background noise and non-specific reactions between components in the liquid specimen and microscopic portions of the carrier not coated with conjugates such as antigens. Such background noise and non-specific reactions have the effect of increasing the apparent magnitude of the reactions occurring on the carrier.

Some systems in the past are believed to have corrected for the occurrence of non-specific reactions by subtracting out from each measurement a fixed value that is assumed to exist. This technique is not entirely satisfactory, however, because it is believed that the amount of such non-specific reactions can vary significantly for a number of specimens.

It should therefore be appreciated that there is a need for a system that measures reactions occurring between a predetermined class of components in a liquid specimen and their corresponding conjugates coated on a carrier, and that accurately corrects for the effects of non-specific and background noise. The present invention fulfills this need.

SUMMARY OF THE INVENTION

The present invention is embodied in an apparatus and related method for measuring the magnitudes of any reactions occurring between a predetermined class of components in a liquid specimen and their corresponding conjugates coated on an insoluble carrier. The carrier includes a plurality of separate test regions, each coated with a different component from the class, and, in addition, includes a negative reference region that is uncoated. The carrier is adapted for simultaneous contact of all of its regions with a liquid specimen possibly containing components from the predetermined class. As a result, any resulting reaction on each test region indicates the specific reaction of a particular component in the class as well as non-specific reactions of such components, and any resulting reaction on the negative reference region indicates non-specific reactions of the class to the carrier.

In accordance with the invention, the apparatus includes measurement means for measuring the magnitude of the reaction occurring on each region of the carrier, including its test regions and its negative reference region, along with adjustment means for adjusting the measurement of each test region in accordance with the measurement of the reference region, to correct for the effects of non-specific reactions and background noise and thereby produce a corrected measurement of the reaction occurring on each test region. Thus, the test region measurements are corrected by an amount that is selected individually for the particular liquid specimen being tested, thereby providing a significantly more accurate measurement of the specific reactions that result.

The apparatus of the invention is particularly suited for use in detecting allergic reactions by measuring the magnitudes of immunological binding reactions occurring between immunoglobulin components present in the liquid specimen, such as IgG, IgA, IgM, IgD, IgE, and their subclasses and coated test regions on a carrier. These regions can advantageously take the form of separate cotton threads, each coated with a different binding conjugate for the immunoglobulin component whose presence is to be detected and measured.

In such applications, the apparatus preferably includes comparator means for comparing the measurement of the binding reaction occurring on each test region with a plurality of predetermined thresholds, to categorize each binding reaction into one of a plurality of reaction categories. The adjustment means preferably reduces each test region measurement by an amount determined by the measurement of the reference region. The apparatus preferably further includes printer means for printing the reaction categories determined for the various test regions.

In another aspect of the invention, the measurement means includes means for producing a photographic positive print or negative having a plurality of separate stripes or spots, each corresponding to a different region on the carrier. The optical density of each spot represents the magnitude of the reaction occurring on the corresponding carrier region, and the measurement means further includes optical density means for measuring the optical density of each spot. The separate spots are preferably spaced from each other in a linear array, and the measurement means further includes transport means for moving the photographic print in a linear direction relative to the optical density means, to permit individual measurement of each spot.

To reduce the effects of individual variations in the measurement of the reaction occurring on each carrier region, the carrier can include a plurality of uncoated negative reference regions. The measurement means of the apparatus measures the magnitude of the reaction occurring on each of such negative reference regions, and the adjustment means averages these measurements and adjusts each test region measurement in accordance with the average. The carrier can further include a positive reference region having a reaction selected to be within a prescribed range. This can be accomplished, for example, by coating the region with a prescribed concentration of a component or components in the predetermined class. To utilize this positive reference region, the measurement means of the apparatus measures the magnitude of the binding reaction occurring on it and the apparatus further includes means for comparing the measurement with a prescribed threshold and generating a flag signal in accordance with the outcome.

Other aspects and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIG. 5 is a simplified flowchart of the operational steps implemented by the microprocessor included in the block diagram of FIG. 4.

DESCRIPTION OF THE PREFERRED EMBODIMENT

Figure 1:
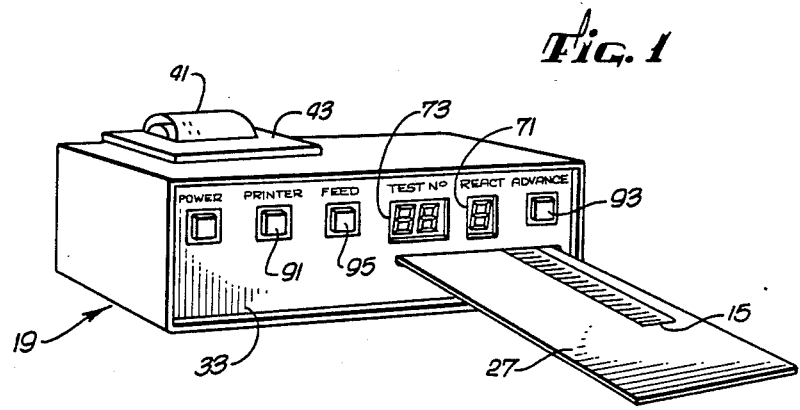
FIG. 1 is a perspective view of a scanning densitometer apparatus embodying the invention, for measuring the optical densities of a number of separate spots on a reader card.
Figure 2:
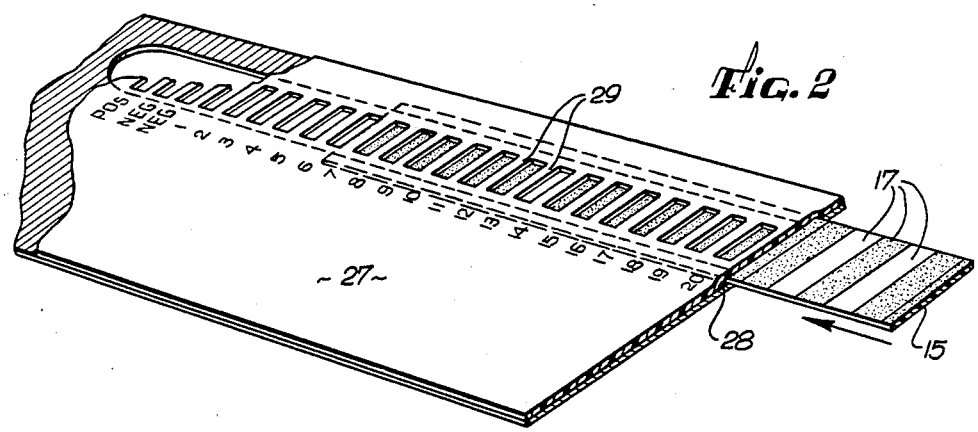
FIG. 2 is a fragmentary perspective view of the reader card adapted for insertion into the densitometer apparatus of FIG. 1, the card including a strip of photographic film having a linear series of transverse stripes whose optical densities are to be measured by the apparatus.
Figure 3:
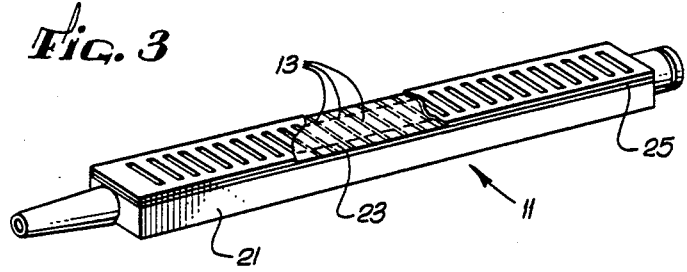
FIG. 3 is a perspective view of an elongated carrier having a plurality of transverse threads coated with binding components such as allergens, for use in producing the photographic film strip shown in FIG. 2.

Referring now to the drawings, and particularly to FIGS. 1, 2 and 3, there is shown a system for measuring the binding reactions occurring between a class of components such as immunoglobulin E (IgE) in a liquid specimen and their corresponding binding conjugates, i.e., allergens, coated on a carrier 11. The carrier includes a number of cotton test threads 13 coated with different allergens and adapted for simultaneous contact with the liquid specimen.

As will be described in greater detail below, carrier 11 can be used to produce a strip of photographic film 15 having a linear array of transverse spots or stripes 17, each having an optical density indicating the magnitude of the reaction for a particular test thread 13. A scanning densitometer 19 successively measures the optical density of each such film stripe, to provide an indication of a patient's reaction to various allergens.

The scanning densitometer 19 compares its measurement of each region on the photographic film 15 with a number of predetermined thresholds, to categorize the binding reaction it represents into one of several reaction categories. For example, these categories can be the conventional reaction categories designated 0, 0/1, 1, 2, 3 or 4.

The binding reaction occurring on each test thread 13 represents not only the binding of the particular IgE component that is specific to the allergen coated on it, but also non-specific binding of various serum components to the thread itself. Background noise, including variations in the opacity of the substrates of different strips of film, also interferes with the measurement of specific binding. Since allergists are ordinarily interested only in the magnitude of the allergen-specific binding reaction, the occurrence of background noise and non-specific binding interferes with its measurement.

In accordance with the invention, at least one of the threads 13 on the carrier 11 is designated a negative reference thread and is not coated with any allergen, so that the presence of IgE on it after incubation with the liquid specimen indicates the magnitude of non-specific binding to the thread. The scanning densitometer 19 measures the magnitude of the optical density of the film stripe 17 corresponding to this negative reference thread and then adjusts its measurements of the film stripes 17 that correspond to allergen-coated test threads. This corrects for the effects of non-specific binding and background noise on those measurements, and thus greatly improves the accuracy of the system in determining a patient's reaction to each allergen.

Referring now specifically to FIG. 3, the preferred carrier 11 is shown to include a rigid body 21 having an elongated, shallow test chamber 23, along with approximately 30 cotton threads 13 stretched in spaced parallel relationship across the top of the chamber, and with a two-part cover 25 for enclosing the chamber and threads. All but a few of the threads are designated to be test threads, i.e., are individually coated with prescribed concentrations of various allergens. The carrier is described in detail In a copending and commonly-assigned application for U.S. Patent, Ser. No. 476,367, filed in the names of William J. Sell, et al., and entitled "Binding Assay System And Method Of Making And Using Same".

In use, a patient's blood serum is introduced into the test chamber 23, where it incubates with the reference and test threads 13 for a prescribed time duration. Any IgE present in the serum that is specific to a particular allergen coated on a particular test thread will bind directly to that allergen and, in addition, some serum components will bind non-specifically to the cotton threads themselves.

In the preferred system, the presence of IgE on each thread 13 is detected using a radioimmunoassay technique in which a solution containing radioactively-tagged anti-IgE is introduced into the test chamber 23, for incubation with the threads. As a result, the threads are all radioactively tagged in accordance with the susceptibility of a patient to the corresponding allergens.

For convenience in measuring the amount of radioactivity on each thread 13, the carrier 11 is used to expose a pattern in the strip of photographic film 15. The resulting exposure pattern includes a linear sequence of spaced, transverse stripes 17, the optical density of each indicating the amount of radioactivity present on the corresponding thread. The prescribed duration of the exposure is determined in accordance with the strength of the radioactive solution, as well as the temperature at which the exposure takes place.

The resulting strip of photographic film 15 is trimmed and placed in a special reader card 27 having a paper backing and a transparent plastic coversheet with a pocket 28 for holding the film. The portion of the coversheet immediately overlaying the film has a series of dark index lines 29 for separating the successive transverse stripes 17 on the film. This film holding card is described in detail in a copending and commonly-assigned application for U.S. Patent, Ser. No. 483,291, filed simultaneously with this application in the names of Gary B. Krantz and Christopher A. Conde, entitled "Reader Card for Densitometric Test Analysis". This referenced application is incorporated by reference.

The film-holding card 27, with the photographic film 15 in place, is inserted through a slot 31 in the front panel 33 of the scanning densitometer 19. The densitometer moves the card incrementally past a light emitting diode 35 and associated photosensor 37 (shown only in FIG. 4), to measure the light transmitted through the successive stripes 17 on the film. In addition, the densitometer compares the light transmission measurement for each stripe with a number of predetermined thresholds, to categorize the corresponding reaction into its appropriate reaction category. Finally, the densitometer displays the successive reaction category determinations on an LED display 39 and simultaneously prints out the same information on a paper tape 41 using a thermal printer 43.

Figure 4:
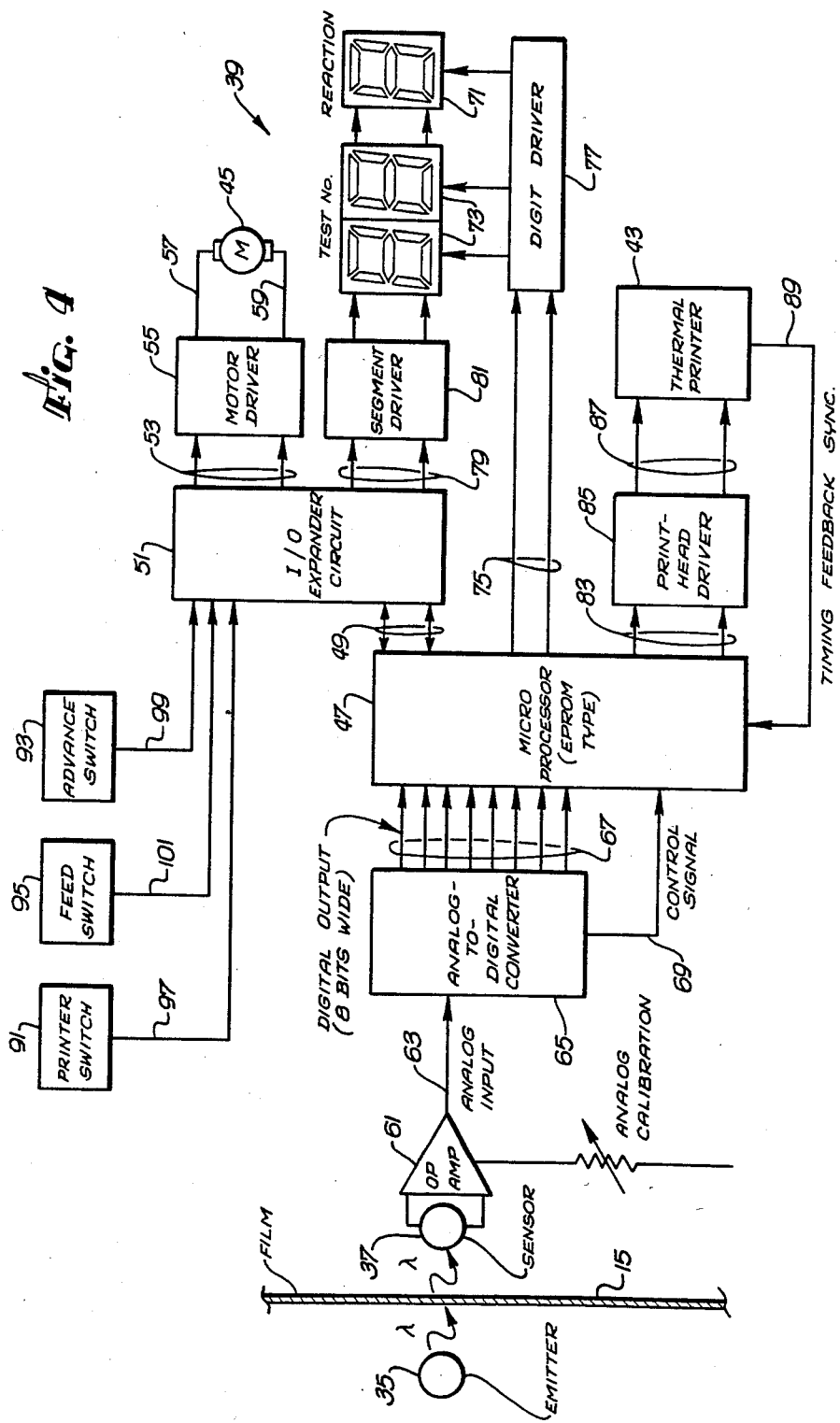
FIG. 4 is a simplified block diagram of the densitometer apparatus of FIG. 1, for measuring the optical density of each region on the reader card of FIG. 2 and for adjusting each such measurement and printing out its appropriate reaction category.

Referring now to FIG. 4, there is shown a simplified block diagram of the scanning densitometer 19. It includes a reversible dc motor 45 for advancing the card 27 and film 15 incrementally past the light emitting diode 35 and photosensor 37. A microprocessor 47 suitably processes the successive light intensity measurements for the transverse stripes 17 on the film, to determine the appropriate reaction categories for the corresponding coated threads 13. The microprocessor also outputs appropriate signals to the LED display 39 and the thermal printer 43, to indicate the successive reaction categories determined for each thread.

The microprocessor 47 advances the card 27 one step by outputting an appropriate signal on lines 49 for coupling through an input/output expander circuit 51 and on lines 53 to a motor drive logic circuit 55. This circuit, in turn, outputs a dc motor drive signal on lines 57 and 59, to advance the dc motor 45, and thus the card 27 and film 15, by an amount equal to the spacing between the index lines 29 separating adjacent stripes.

The light emitting diode 35 and the photosensor 37 are arranged on opposite sides of the advancing card 27, such that the photosensor measures the transmission of light through the film 15. The photosensor is disposed behind a narrow aperture (not shown) such that it senses light transmitted only through a narrow portion of the film stripe 17 disposed immediately adjacent to it. The light intensity measurements output by the photosensor are amplified by an operational amplifier 61 and, in turn, coupled over line 63 to an analog-to-digital converter 65 for conversion into a sequence of 8-bit words. These digitized words are input to the microprocessor 47 on lines 67, under the control of a control signal coupled to the analog-to-digital converter on line 69 from the microprocessor.

The analog-to-digital converter 65 preferably inputs numerous (e.g., 1000) 8-bit digital words to the microprocessor 47 for each stripe 17 on the film 15. The microprocessor detects the highest-valued word in each set, to determine the peak value of light transmission for each stripe. In addition, the microprocessor monitors the successive digital words to detect when the card 27 has been advanced to the point where the photosensor 37 is adjacent the dark index line 29 separating the current stripe from the next succeeding stripe. When this index mark is detected, the microprocessor terminates the motor drive signal, to stop further advancement of the card 27. The index mark is preferably detected by comparing the successive 8-bit words with a particular threshold that is selected in accordance with an optical density measurement for the portion of the card that is scanned when first inserted into the densitometer 19.

The microprocessor 47 is suitably programmed to compare the digitized light intensity measurement for each stripe 17 with a number of predetermined thresholds, to categorize the binding reaction it represents into one of a number of reaction categories. In accordance with conventional standards for characterizing allergic reactions, these thresholds are geometrically related to each other.

Before comparing the peak measurement for each test thread 13 with the set of thresholds, the microprocessor 47 adjusts the measurement to correct for the interfering effects of non-specific binding and background noise. The amount of this adjustment is determined using two negative reference threads that are not coated with any allergens. Thus, any radioactivity that is detected for these threads indicates the occurrence and magnitude of non-specific binding. The measurements for the two film stripes 17 corresponding to these two negative reference threads are averaged and this average number is subtracted from each test thread measurement to produce a corrected measurement. The corrected measurement is then compared to the set of thresholds, to determine the appropriate reaction category for each test thread.

The system also performs a test to verify the accuracy of the measurements for the various test threads 13. This is achieved using a positive reference thread, which is coated directly with IgE itself, rather than with an allergen. Thus, when the carrier 11 is incubated with the radioactively-tagged anti-IgE, a binding reaction will occur with the bound IgE. The concentration of IgE on the thread is preferably selected to provide an amount of radioactivity that corresponds to a reaction category of 2 or greater. If the densitometer's measurement for that thread fails to exceed the threshold for reaction category 2, it is deduced that a test error of some kind has occurred. Possible errors include, for example, using an anti-IgE solution that is too old, i.e., has decayed too much, or exposing the film for too short a duration. When the microprocessor detects such an error, it causes the display 39 to blink and the printer 43 to print an asterisk along with each reading.

The display 39 preferably includes a single seven-segment LED device 71 for indicating the successive reaction category determinations, and a pair of seven-segment LED devices 73 for indicating the number indicating the identity of the particular thread 13 corresponding to each such determination. The microprocessor 47 controls these devices by outputting appropriate control signals over lines 75 to a digit driver circuit 77, and over lines 49 to the input/output expander circuit 51, which relays the signals over lines 79 to a segment driver circuit 81 for driving the LED devices. The digit driver circuit permits time multiplexing of the LED devices 71 and 73, so as to minimize microprocessor output connections. The reaction is preferably displayed as a single digit 0, 1, 2, 3 or 4, and the test identification number is preferably displayed as a two digit number ranging as high as about 30, corresponding to the number of test threads 13 on the carrier 11.

As previously mentioned, the system provides a paper tape read-out of the reaction category for each test thread 13 using a thermal printer 43. In particular, the microprocessor 47 outputs appropriately-formatted control signals for coupling on lines 83 to a print head driver 85, which drives the printer by means of lines 87. A timing feedback synchronization signal is coupled back to the microprocessor from the printer on line 89, to indicate when each printing cycle has been completed.

Several control switches on the front panel 33 (FIG. 1) of the scanning densitometer 19 are useful in sequencing it through its operations. These switches include a mode or printer switch 91, an advance switch 93 and a feed switch 95. The binary signals from each are input to the microprocessor 47 on lines 97, 99 and 101, respectively, through the input/output expander circuit 51.

The printer switch 91 selects one of two operating modes for the system. In one such mode, the thermal printer 43 is enabled, and the system automatically sequences through the successive stripes 17 on the film 15. In this mode, the reversible dc motor 45 advances the card 27 by one step immediately after the preceding printing cycle has been completed. In the second operating mode selected by the printer switch, the printer 43 is disabled, and the LED display 39 provides a continuous display of the reaction category for the current film stripe until the advance switch 93 is actuated, instructing the microprocessor 47 to advance the motor by one step. The feed switch 95 is useful in selectively advancing the paper tape 41 associated with the thermal printer.

Referring now to FIG. 5, there is shown a simplified flowchart of the operational steps performed by the microprocessor 47 in guiding the system through its measurement of the successive film stripes 17 and displaying and printing out the reaction category determined for each. In an initial step 103, the microprocessor clears its various internal registers and enables the LED display 39 by outputting appropriate control signals on lines 75 to the digit driver circuit 77 and on lines 49 to the segment driver circuit 81. It is then determined at step 105 whether or not a card 27 has been inserted into the slot 31 of the densitometer 19. If it has not, the program advances to a step 107 where it is determined whether or not the thermal printer 43 has been enabled by the mode switch 91. If not enabled, the program returns to the card determination step 105, whereas if the printer has been enabled, the program proceeds to step 109 where it is determined whether or not the feed switch 95 has been actuated. If it has been actuated, the microprocessor outputs an appropriate signal to feed the printer paper 41 by one line at step 111. After this has been done, or if the feed switch has not been actuated, the program returns to the initial card determination step 105.

Once it has been determined at step 105 that a card 27 has been inserted into the densitometer 19, the program advances to step 113, where the microprocessor 47 disables the LED display 39 and advances the dc motor 45 to move the first three stripes 17 on the film 15 past the photosensor 37. The microprocessor reads and stores the peak value of the first stripe 17 at step 113, reads and stores the peak value for the second stripe at step 115, and finally reads the peak value of the third stripe at step 117. These first three stripes correspond to the first three threads 13 on the carrier 11. The second and third threads are the two negative reference threads are not coated with any allergens, so any film exposure for the corresponding second and third stripes represents the level of non-specific binding for this particular serum sample. In step 117, the microprocessor also averages the readings for the second and third stripes. If desired, this average can be compared with a predetermined maximum value, and if the value is exceeded, a determination made that the ensuing test results are of questionable validity.

Thereafter, in step 119, the microprocessor 47 adjusts the stored measurement for the first thread 13, which is the positive reference thread described above, by subtracting from it a number equal to the calculated level of non-specific binding. This level is determined in accordance with the average measurement of the two negative reference threads, determined in step 117. Also in step 119, the microprocessor compares the corrected measurement for the first stripe with the threshold for the reaction category of 2. If the reading fails to exceed the threshold, it is determined that the subsequent test readings will be of questionable accuracy, and the microprocessor, at step 121, sets an internal flag, causing the LED display 71 to blink and the thermal printer 43 to print an asterisk on each line it prints out.

After the flag has been set at step 121, or after it has been determined at step 119 that the measurement for the first thread 13 does indeed exceed the prescribed threshold, the program advances to step 123, where the card 27 is advanced by one increment and the peak light intensity measurement for the next stripe is detected and stored. Also in step 123, the microprocessor 47 adjusts the peak measurement to correct for non-specific binding. As was the case with the positive reference thread, this is accomplished by subtracting from the measurement the number equal to the average measurement for the two negative reference threads. The adjusted measurement is then compared with the various reaction category thresholds, to determine the appropriate category for the thread, and an internal position register is incremented, to indicate the identity of the particular thread just measured.

The microprocessor 47 thereafter determines at step 125 whether or not its internal position register has been advanced to the number 28, which would indicate that the entire film strip 15 has been scanned. If not, the microprocessor, at step 127, updates the test number and reaction category displayed on the LED display 39 so that it displays the information for the current stripe 17. It is then determined at step 129 whether or not the printer 43 has been enabled. If it has, the microprocessor, at step 131, prints the test number and reaction category for the current thread 13 and returns to the step 123 of advancing the card 27. On the other hand, if it is determined that the printer has not been enabled, the program proceeds to step 133 where it remains until the advance switch 93 has been actuated. Only when that occurs does the microprocessor return to the step 123 of advancing the card.

When it is finally determined at step 125 that the card 27 has been advanced to the 28th test position, the program proceeds to step 135 where the dc motor 45 is driven in reverse, to begin ejecting the card, the LED display 39 is disabled, and the internal position register decremented by one count as soon as the previous index line 29 has been reached. This step is repeated until it is determined at step 137 that the internal position register has reached zero. Thereafter, the motor is stopped at step 139 and it is determined at step 141 whether or not the thermal printer 43 has been enabled. If it has, four lines of paper 41 are fed at step 143 and the program then advances to step 145, where it remains until it is determined that the card has been removed from the densitometer 19. Once the card has been removed, the program returns to the initial step 103 of clearing its various registers.

It should be appreciated from the foregoing description that the present invention provides an effective system for measuring the reactions occurring between components of a predetermined class (e.g., IgE) with their corresponding conjugates (e.g., allergens) coated individually on a carrier. In an important feature of this system, it corrects for the interfering effects of background noise and non-specific reaction of the class of components with the carrier. This greatly enhances the accuracy of the reaction determinations made for each component.

Although the invention has been described in detail with reference to the presently preferred embodiment, it should be understood by those of ordinary skill in the art that various modifications can be made without departing from the invention. Accordingly, the invention is limited only by the following claims.

We claim:

1. Apparatus for measuring the magnitudes of reactions occurring between a predetermined class of components in a liquid specimen and a plurality of separate, coated test regions on a carrier, the carrier further including a separate uncoated negative reference region and being adapted for simultaneous contact of its plurality of regions with the liquid specimen, any resulting reaction on each test region indicating both a specific reaction of a particular component in the class of components and non-specific reactions of the class of components, and any resulting reaction on the negative reference region indicating non-specific reactions of the class of components, the apparatus comprising:
   measurement means for measuring the magnitude of the reaction occurring on each test region of the carrier; and
   adjustment means for adjusting the measurement of each test region in accordance with the measurement of the uncoated negative reference region, to correct for the effects of non-specific reactions and thereby produce a corrected measurement of the reaction occurring on each test region.

2. Apparatus as defined in claim 1, wherein the measurement means includes:
   means for producing a photographic print having a plurality of spots, each corresponding to a different test region on the carrier, the optical density of each spot representing the magnitude of the reaction occurring on the corresponding carrier region; and
   optical density means for successively measuring the optical density of each photographic print spot.

3. Apparatus as defined in claim 2, wherein:
   the separate photographic print spots are spaced from each other; and
   the measurement means further includes transport means for moving the photographic print relative to the optical density means, to permit individual measurement of the optical density of each spot.

4. Apparatus as defined in claim 3, wherein:
   the separate photographic print spots are spaced in a linear array; and
   the transport means moves the photographic print in a linear direction relative to the optical density means.

5. Apparatus as defined in claim 1, wherein:
   the carrier includes a plurality of substantially identical uncoated negative reference regions, their reactions indicating the magnitude of non-specific reactions of the predetermined class of components;
   the measurement means measures the magnitude of the reaction occurring on each of the plurality of uncoated negative reference regions; and
   the adjustment means averages the measurements for the plurality of uncoated negative reference regions and adjusts the measurement of each test region in accordance with the average.

6. Apparatus as defined in claim 1, wherein:
   the carrier further includes a positive reference region having a reaction selected to be within a prescribed range;
   the measurement means measures the magnitude of the reaction on the positive reference region; and
   the apparatus further includes means for comparing the measurement of the positive reference region with a prescribed threshold and generating a signal in accordance with the outcome.

7. Apparatus as defined in claim 1, wherein the predetermined class of components is selected from the group consisting of IgG, IgA, IgM, IgD, IgE, and their subclasses.

8. Apparatus as defined in claim 1, and further including comparator means for comparing the corrected measurement of the reaction occurring on each test region with a plurality of predetermined thresholds, to categorize each binding reaction into one of a plurality of reaction categories.

9. Apparatus as defined in claim 8, wherein the adjustment means subtracts from the measurement of each test region a number determined in accordance with the measurement of the uncoated negative reference region.

10. Apparatus as defined in claim 8, and further including printer means for printing the reaction categories determined for the plurality of test regions.

11. Apparatus for measuring the magnitudes of binding reactions occurring between a predetermined class of components in a liquid specimen and a carrier wherein the carrier has a generally elongated support member and a plurality of cotton threads arranged transversely on the support member, in a spaced parallel relationship, the threads including a plurality of test threads coated individually with prescribed concentrations of separate components from the class of components, a positive reference thread coated with a prescribed concentration of a binding conjugate for the class of components, and a negative reference that is uncoated, and wherein the carrier is adapted for simultaneous contact of its plurality of threads with the liquid specimen, any resulting binding reaction on each test thread indicating both specific binding of a particular component in the class of components and non-specific binding of the class of components, and any resulting binding reactin on the negative reference thread indicating non-specific binding of the class of components, the apparatus comprising:

means for producing a photographic print having a linear array of transverse stripes, each having an optical density representing the magnitude of the binding reaction occurring on a particular thread;

optical density means for measuring the optical density of a selected stripe on the photographic print;

transport means for moving the photographic print in a linear direction relative to the optical density means, whereby the optical density means measures the optical density of each stripe in a sequential fashion;

adjustment means for reducing the measurements of the test threads and the positive reference thread in accordance with the measurement of the uncoated negative reference thread, to correct for the effects of non-specific binding and thereby produce a corrected measurement for each thread;

means for comparing the corrected measurement for the positive reference thread with a prescribed threshold and generating a flat signal in accordance with the outcome; and means for comparing the corrected measurement for each test thread with a plurality of predetermined thresholds, to categorize the binding reaction represented by each such thread into one of a plurality of reaction categories.

12. Apparatus for use in the diagnostic analysis of a liquid specimen, comprising:

a carrier having a plurality of substantially identical regions adapted for simultaneous contact with a liquid specimen, the regions including a plurality of test regions and a negative reference region; and a separate assay component from a predetermined class of components coated on each of the plurality of test regions;

wherein the negative reference region is not coated with any assay component;

wherein any conjugate present in the liquid specimen specific to any assay component coated on one of the test regions can react with the component; and wherein conjugates present in the liquid specimen can react non-specifically with both the test regions and the negative reference region of the carrier.

13. Apparatus as defined in claim 12 wherein:
  the carrier is elongated; and
  the plurality of regions of the carrier are cotton threads arranged transversely in a spaced, parallel relationship.

14. Apparatus as defined in claim 12, wherein the carrier includes a plurality of negative reference regions that are substantially identical to each other and are not coated with any assay component.

15. Apparatus as defined in claim 12, wherein:
  the carrier further includes a positive reference region substantially identical to the plurality of test regions and the negative reference region; and
  the positive reference region is coated with a prescribed quantity of one or more conjugates for the predetermined class of components.

16. Apparatus as defined in claim 12, wherein:
  the predetermined class of components are allergens; and
  the binding conjugates present in liquid specimen that can react with the coated carrier are immunoglobulin E.

17. Apparatus for use in the diagnostic analysis of a liquid specimen through binding assays, comprising:

an elongated carrier having a plurality of substantially identical cotton threads arranged transversely, in a spaced parallel relationship, the threads being adapted for simultaneous contact with a liquid specimen and including a plurality of test threads, a positive reference thread and a plurality of negative reference thread;

a prescribed quantity of separate binding assay component from a predetermined class of components coated on each of the plurality of test threads; and a prescribed quantity of a binding conjugate for the predetermined class of components coated on the positive reference thread;

wherein the plurality of negative reference threads are uncoated;

wherein any binding conjugate present in the liquid specimen that is specific to a binding assay component coated on one of the test threads can bind to the component; and wherein binding conjugates present in the liquid specimen can bind non-specifically to the test threads, the positive reference thread and the negative reference threads.

18. A method for measuring the magnitudes of reactions occurring between a predetermined class of components in a liquid specimen and a plurality of separate, coated test regions on a carrier, the carrier further including a separate uncoated negative reference region and being adapted for simultaneous contact of its plurality of regions with the liquid specimen, any resulting reaction on each test region indicating both a specific reaction of a particular component in the class of components and non-specific reactions of the class of components, and any resulting reaction on the negative reference region indicating non-specific reactions of the class of components, the method comprising steps of:

measuring the magnitude of the reaction occurring on each region of the carrier; and adjusting the measurement of each test region in accordance with the measurement of the uncoated negative reference region, to correct for the effects of non-specific reactions and thereby produce a corrected measurement of the reaction occurring on each test region.

19. A method defined in claim 18, wherein the step of measuring includes steps of:

producing a photographic print having a plurality of spots, each corresponding to a different region on the carrier, the optical density of each spot representing the magnitude of the reaction occurring on the corresponding carrier region; and measuring the optical density of each photographic print spot using a photosensor.

20. A method as defined in claim 19, wherein:
  the separate photographic print spots are spaced from each other; and
  the step of measuring further includes a step of moving the photographic print relative to the photosensor, to permit individual measurement of the optical density of each spot.

21. A method as defined in claim 20, wherein:

the separate photographic print spots are spaced in a linear array; and the step of moving moves the photographic print in a linear direction relative to the photosensor.

22. A method as defined in claim 18, wherein:

the carrier includes a plurality of substantially identical negative reference regions, their reactions indicating the magnitude of non-specific reactions of the predetermined class of components;

the step of measuring measures the magnitude of the reaction occurring on each of the plurality of uncoated negative reference regions; and the step of adjusting averages the measurements for the plurality of negative reference regions and adjusts the measurement of each test region in accordance with the average.

23. A method as defined in claim 18, wherein:

the carrier further includes a positive reference region having a reaction selected to be within a prescribed range;

the step of measuring measures the magnitude of the reaction on the positive reference region; and the method further includes a step of comparing the measurement of the positive reference region with a prescribed threshold and generating a signal in accordance with the outcome.

24. A method as defined in claim 18, wherein the predetermined class of components is selected from the group consisting of IgG, IgA, IgM, IgD, IgE, and their subclasses.

25. A method as defined in claim 18, and further including a step of comparing the corrected measurement of the reaction occurring on each test region with a plurality of predetermined thresholds, to categorize each binding reaction into one of a plurality of reaction categories.

26. A method as defined in claim 25, wherein the step of adjusting subtracts from the measurement of each test region a number determined in accordance with the measurement of the uncoated negative reference region.

27. A methods as defined in claim 25, and further including a step of printing the reaction categories determined for the plurality of test regions.

* * * * *